(12) United States Patent  (10) Patent No.: US 7,674,284 B2
Melsheimer  (45) Date of Patent: Mar. 9, 2010

(54) ENDOLUMINAL GRAFT

(75) Inventor: Jeffry Scott Melsheimer, Springville, IN (US)

(73) Assignee: Cook Incorporated, Bloomington, IN (US)

( * ) Notice: Subject to any disclaimer, the term of this patent is extended or adjusted under 35 U.S.C. 154(b) by 991 days.

(21) Appl. No.: 11/090,534

(22) Filed: Mar. 25, 2005

(65) Prior Publication Data

US 2005/0234542 A1  Oct. 20, 2005

(51) Int. Cl.
A61F 2/06 (2006.01)

(52) U.S. Cl. ..................... 623/1.35; 623/1.13

(58) Field of Classification Search .............. 623/1.1, 623/1.35, 1.36, 137; 606/191–198
See application file for complete search history.

(56) References Cited

U.S. PATENT DOCUMENTS

| | | | |
|---|---|---|---|
| 4,994,071 A | 2/1991 | MacGregor | |
| 5,135,536 A | 8/1992 | Hillstead | |
| 5,197,976 A * | 3/1993 | Herweck et al. | 623/1.27 |
| 5,489,295 A | 2/1996 | Piplani et al. | |
| 5,507,769 A | 4/1996 | Marin et al. | |
| 5,562,724 A | 10/1996 | Vorwerk et al. | |
| 5,575,817 A | 11/1996 | Martin | |
| 5,591,195 A | 1/1997 | Taheri et al. | |
| 5,609,627 A | 3/1997 | Goicoechea et al. | |
| 5,632,763 A | 5/1997 | Glastra | |
| 5,676,697 A * | 10/1997 | McDonald | 623/1.35 |
| 5,683,451 A | 11/1997 | Lenker et al. | |
| 5,709,713 A | 1/1998 | Evans et al. | |
| 5,713,917 A | 2/1998 | Leonhardt et al. | |
| 5,755,773 A | 5/1998 | Evans et al. | |
| 5,769,882 A | 6/1998 | Fogarty et al. | |
| 5,782,906 A | 7/1998 | Marshall et al. | |
| 5,824,040 A | 10/1998 | Cox et al. | |
| 5,893,887 A | 4/1999 | Jayaraman | |
| 5,904,713 A | 5/1999 | Leschinsky | |
| 5,961,548 A | 10/1999 | Shmulewitz | |
| 6,033,434 A | 3/2000 | Borghi | |
| 6,039,749 A | 3/2000 | Marin et al. | |
| 6,051,020 A | 4/2000 | Goicoechea et al. | |
| 6,056,775 A | 5/2000 | Borghi et al. | |

(Continued)

FOREIGN PATENT DOCUMENTS

EP  0 880 948 A1  12/1998

(Continued)

OTHER PUBLICATIONS

Kubota, Y. et al.; "Bilateral Internal Biliary Drainage of Hilar Cholangiocarcinoma with Modified Gianturco Z Stents Inserted via a Single Percutaneous Tract;" 1993 JVIR 4:605-610.

(Continued)

Primary Examiner—Kevin T Truong
(74) Attorney, Agent, or Firm—Brinks Hofer Gilson & Lione

(57) ABSTRACT

An endoluminal graft includes a unitary tube of graft material forming two adjacent legs that are integral and monolithic to each other. The graft can be part of a prosthesis assembly for treatment of branched vascular systems and can function as an integral bifurcated leg extension prosthesis in combination with a main bifurcated prosthesis. In treating abdominal aortic aneurysms, the graft can be deployed within both iliac arteries.

17 Claims, 7 Drawing Sheets

U.S. PATENT DOCUMENTS

| | | | |
|---|---|---|---|
| 6,068,655 | A | 5/2000 | Seguin et al. |
| 6,077,297 | A | 6/2000 | Robinson et al. |
| 6,093,203 | A | 7/2000 | Uflacker |
| 6,102,938 | A | 8/2000 | Evans et al. |
| 6,110,198 | A | 8/2000 | Fogarty et al. |
| 6,110,201 | A * | 8/2000 | Quijano et al. ............... 623/2.1 |
| 6,117,167 | A | 9/2000 | Goicoechea et al. |
| 6,129,756 | A | 10/2000 | Kugler et al. |
| 6,143,002 | A | 11/2000 | Vietmeier |
| 6,183,509 | B1 | 2/2001 | Dibie |
| 6,197,049 | B1 | 3/2001 | Shaolian et al. |
| 6,200,339 | B1 | 3/2001 | Leschinsky et al. |
| 6,245,102 | B1 | 6/2001 | Jayaraman |
| 6,283,991 | B1 | 9/2001 | Cox et al. |
| 6,299,634 | B1 | 10/2001 | Bergeron |
| 6,306,164 | B1 | 10/2001 | Kujawski |
| 6,325,819 | B1 | 12/2001 | Pavcnik et al. |
| 6,344,056 | B1 | 2/2002 | Dehdashtian |
| 6,355,061 | B1 | 3/2002 | Quiachon et al. |
| 6,368,345 | B1 | 4/2002 | Dehdashtian et al. |
| 6,395,022 | B1 | 5/2002 | Piplani et al. |
| 6,409,757 | B1 | 6/2002 | Trout, III |
| 6,416,542 | B1 | 7/2002 | Marcade et al. |
| 6,436,134 | B2 | 8/2002 | Richter et al. |
| 6,454,796 | B1 | 9/2002 | Barkman et al. |
| 6,464,720 | B2 | 10/2002 | Boatman |
| 6,475,208 | B2 | 11/2002 | Mauch |
| 6,478,813 | B1 | 11/2002 | Keith et al. |
| 6,508,836 | B2 | 1/2003 | Wilson et al. |
| 6,524,335 | B1 | 2/2003 | Hartley et al. |
| 6,524,336 | B1 | 2/2003 | Papazolgou et al. |
| RE38,146 | E | 6/2003 | Palmaz et al. |
| 6,576,009 | B2 | 6/2003 | Ryan et al. |
| 6,585,753 | B2 | 7/2003 | Eder et al. |
| 6,602,225 | B2 | 8/2003 | Eidenschink et al. |
| 6,666,883 | B1 | 12/2003 | Seguin et al. |
| 6,673,107 | B1 | 1/2004 | Brandt et al. |
| 6,695,875 | B2 | 2/2004 | Stelter et al. |
| 6,695,877 | B2 | 2/2004 | Brucker et al. |
| 6,827,735 | B2 | 12/2004 | Greenberg |
| 6,860,900 | B2 | 3/2005 | Clerc et al. |
| 6,878,161 | B2 | 4/2005 | Lenker |
| 7,131,991 | B2 | 11/2006 | Zarins et al. |
| 2001/0027338 | A1 | 10/2001 | Greenberg |
| 2002/0042644 | A1 | 4/2002 | Greenhalgh |
| 2002/0120233 | A1 | 8/2002 | Eidenschink et al. |
| 2002/0156517 | A1 | 10/2002 | Perouse |
| 2002/0156521 | A1 | 10/2002 | Ryan et al. |
| 2002/0156522 | A1 | 10/2002 | Ivancev et al. |
| 2002/0198585 | A1 | 12/2002 | Wisselink |
| 2002/0198587 | A1 | 12/2002 | Greenberg et al. |
| 2003/0097169 | A1 | 5/2003 | Brucker et al. |
| 2003/0149473 | A1 | 8/2003 | Chouinard et al. |
| 2003/0158594 | A1 | 8/2003 | Kang et al. |
| 2003/0199967 | A1 | 10/2003 | Hartley et al. |
| 2003/0220682 | A1 | 11/2003 | Kujawski |
| 2004/0054404 | A1 | 3/2004 | Wilson et al. |
| 2004/0082990 | A1 | 4/2004 | Hartley |
| 2004/0111148 | A1 | 6/2004 | Goodson |
| 2004/0153147 | A1 | 8/2004 | Mathis |
| 2004/0167616 | A1 | 8/2004 | Camrud |
| 2004/0176833 | A1 | 9/2004 | Pavcnik et al. |
| 2004/0210306 | A1 | 10/2004 | Quijano et al. |
| 2004/0230287 | A1 | 11/2004 | Hartley et al. |
| 2004/0243221 | A1 | 12/2004 | Fawzi et al. |
| 2005/0177222 | A1 | 8/2005 | Mead |
| 2005/0234542 | A1 | 10/2005 | Melsheimer |
| 2006/0089704 | A1 | 4/2006 | Douglas |
| 2006/0161244 | A1 | 7/2006 | Seguin |
| 2006/0178726 | A1 | 8/2006 | Douglas |

FOREIGN PATENT DOCUMENTS

| | | |
|---|---|---|
| WO | WO 98/07389 | 2/1998 |
| WO | WO 98/44870 | 10/1998 |
| WO | WO98/53761 | 12/1998 |
| WO | WO 2002/067815 | 9/2002 |
| WO | WO 2003/065933 | 8/2003 |
| WO | WO 2003/082153 | 10/2003 |
| WO | WO 2004/100836 | 11/2004 |

OTHER PUBLICATIONS

U.S. Appl. No. 11/014,669 filed on Dec. 16, 2004.
US 6,413,270, 07/2002, Thornton et al. (withdrawn)

* cited by examiner

ENDOLUMINAL GRAFT

TECHNICAL FIELD

This invention relates to endoluminal grafts and prostheses for implantation within the human or animal body for the repair of damaged lumens such as blood vessels.

BACKGROUND

The functional vessels of human and animal bodies, such as blood vessels and ducts, occasionally weaken or even rupture. For example, in the aortic artery, the vascular wall can weaken or tear, resulting in dangerous conditions such as aneurysm and dissection. Treatment of such conditions can be performed by implanting a prosthesis within the vascular system using minimally invasive surgical procedures. An endoluminal prosthesis typically includes one or more stents affixed to graft material and is delivered to the treatment site by endovascular insertion. Once the endoluminal prosthesis is radially enlarged, it should remain in place indefinitely by self-attachment to the vessel wall, acting as a substitute vessel for the flow of blood or other fluids.

Treatment of vascular conditions near a branch point with an endoluminal prosthesis can present a number of difficulties. A single, straight section of a tubular prosthesis may not be able to span the length of the aneurysm or dissection and still maintain sufficient contact with healthy vascular tissue to secure the prosthesis and to prevent endoleaks. For example, most abdominal aortic aneurysms occur at or near the iliac bifurcation, and treatment with an endoluminal prosthesis requires the presence of prosthesis material in the main aorta and in the iliac branch arteries (Dietrich, E. B. *J. Invasive Cardiol.* 13(5):383-390, 2001). Typically, an endoluminal prosthesis for use near a bifurcation will have a main lumen body, for placement within the aorta, and two branch lumens extending from the main lumen body into the branch arteries.

A simple approach to bifurcated prostheses from a materials perspective is to use a unitary prosthesis. Such unitary structures have a main tubular body and pre-formed leg extensions. The seamless structure provided by this configuration can minimize the probability of leakage within the prosthesis. However, the constrained geometry of branched vasculature makes it extremely-difficult to deliver such a large structure to the treatment site. For example, in treating aortic aneurysms, the deployment of a leg extension down the contralateral iliac artery is especially problematic.

A more common alternative to the single piece approach is the use of a modular system. In these systems, one or both of the leg extensions can be attached to limb portions of a main bifurcated tubular body to provide the final prosthesis. Examples of modular systems are described in PCT Patent Application Publication WO98/53761 and in U.S. Patent Application Publication 2002/0198587 A1, which are incorporated herein by reference. Although the delivery of modular systems is less difficult due to the smaller sizes of the individual components, it can still be a complex and time-consuming process to make the precise connections between the body and one or both legs. The difficulty and risk of the treatment procedure can also increase when there are more individual parts to insert, align, and deploy. Possible complications with modular systems include the occurrence of endoleaks, due to imperfect seals between the body and a leg component, and the separation of the legs from the main prosthesis body over time.

BRIEF SUMMARY

In one aspect of the invention, there is a unitary endoluminal graft, comprising a flexible tube having a first tubular section, a second tubular section, a weakened section, which upon separating or bending the tube at the weakened section provides an integral graft having adjacent legs that are integral to and monolithic with each other.

In another aspect of the invention, there is an endoluminal prosthesis assembly comprising a main body having a proximal end and a distal end; and a tube of graft material insertable into at least one of the proximal and distal ends, the tube of graft material comprising a weakened second, a first leg disposed adjacent one side of the weakened section, and a second leg integral with and adjacent to the first leg and disposed adjacent the other side of the weakened section.

In another aspect of the invention, a method is provided for making a unitary bifurcated endoluminal graft comprising, forming a tube of biocompatible graft material; forming a weakened section in the graft material on a side of the tube; and laterally bending the tube at the weakened section in a direction opposite the weakened section to create two adjacent and integrally connected tubular sections.

In yet another aspect of the invention, a method of repairing a compromised section of a blood vessel is provided, comprising inserting into the aortic artery a bifurcated prosthesis comprising a main tubular body having a single proximal opening, a first distal opening and a second distal opening; introducing a unitary tubular graft having a weakened section, a first tube section adjacent one side of the weakened section, a second tube section adjacent the other side of the weakened section, into a first iliac artery; inserting at least the first section of the tubular graft and through the first distal opening of the main tubular body and into the main tubular body; advancing the first section of the tube through the second distal opening of the main body and partially into the second iliac artery; positioning the weakened section of the tube approximately adjacent the main body bifurcation with the weakened section opposed the bifurcation; separating the tubular graft at the weakened section sufficient to form two adjacent legs and two leg openings at the weakened section; and expanding the tubular graft such that the first section engages the second distal opening of the main body and the second iliac artery and the second section engages the first distal opening of the main body and the first iliac artery.

These aspects may further include a plurality of self-expanding stents attached to the graft material at various regions of the graft material.

DETAILED DESCRIPTION

The present invention relates to a unitary bifurcated endoluminal graft that is constructed from a single tube of graft material. The graft includes a tube of graft material having a longitudinal axis and a weakened section at a point along the length of the graft. The weakened section may comprise a lateral cut or a series of perforations that are perpendicular to the longitudinal axis of the graft. The weakened section may be located at any point on the graft. Preferably, the weakened section is a lateral cut and is located roughly midway between the two ends of the graft tube to form two tube sections of substantially the same length on either side of the weakened section.

The weakened section may be of sufficient length to permit the separation of the tube section into adjacent legs by bending the tube at the weakened section, but not so long as to sever the tube sections into separate components. Thus, opposite the weakened section and integral to the tube sections is portion of the graft material that maintains the unitary nature of the graft.

The graft tube can be coordinated with a bifurcated prosthesis to form leg portions of an endoluminal prosthesis assembly. In the treatment of an aortic aneurysm, the prosthesis can be delivered through one iliac artery, into a main bifurcated prosthesis, and into the other iliac artery.

Throughout this specification, when discussing the application of this invention to the aorta, the term distal with respect to a prosthesis is intended to refer to the end of the prosthesis furthest away in the direction of blood flow from the heart, and the term proximal is intended to mean the end of the prosthesis that, when implanted, would be nearest to the heart.

The term "prosthesis" means any replacement for a body part or for a function of that body part; or any device that enhances or adds functionality to a physiological system.

The term "endoluminal" describes objects that are found or can be placed inside a lumen or space in the human or animal body. This includes lumens such as blood vessels, parts of the gastrointestinal tract, ducts such as bile ducts, parts of the respiratory system, etc. "Endoluminal prosthesis" thus describes a prosthesis that can be placed inside one of these lumens.

The term "graft" means a generally cannular or tubular member which acts as an artificial vessel. A graft by itself or with the addition of other elements can be an endoluminal prosthesis.

The term "stent" means any device or structure that adds rigidity, radial force or support to a prosthesis. Typically, a stent has a tubular shape when used for endoluminal applications.

Figure 3:
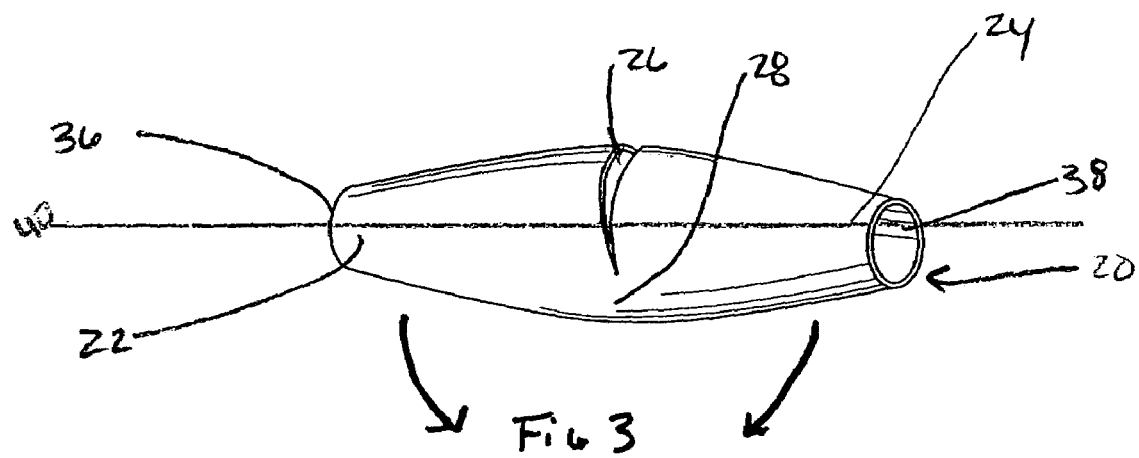
FIG. 3 shows a unitary tubular graft having tapered graft sections and a cut weakened section.
Figure 4:
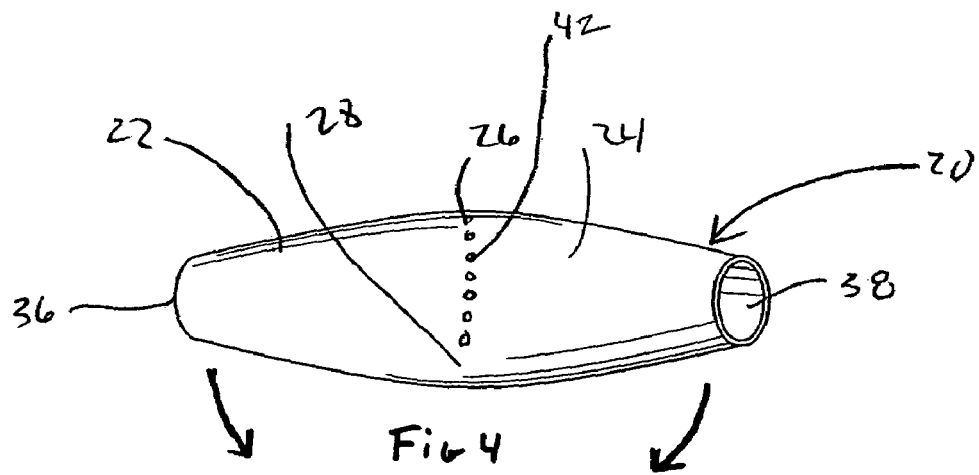
FIG. 4 shows a unitary tubular graft having tapered graft sections and a perforated weakened section.
Figure 5:
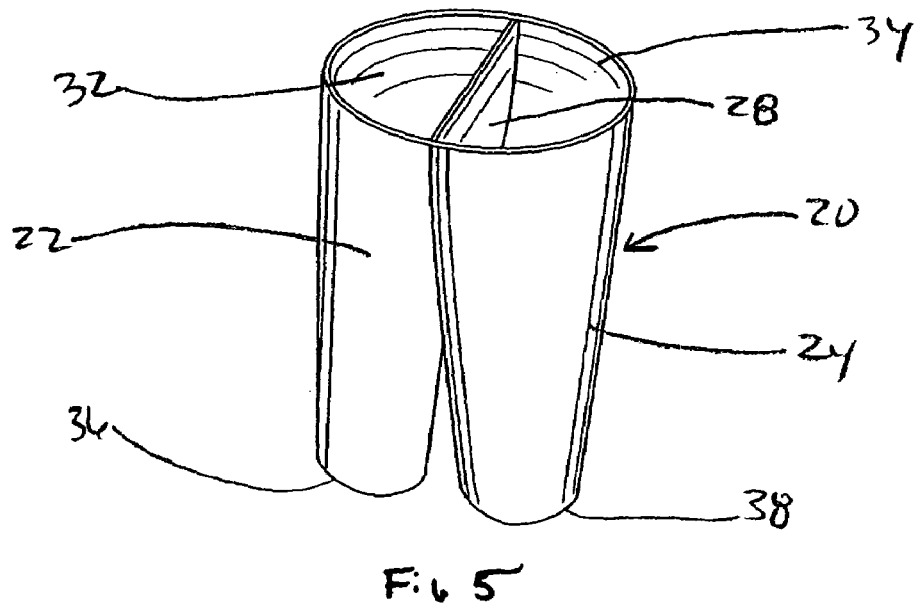
FIG. 5 is a perspective view of the graft of either FIG. 3 or 4 formed into a unitary bifurcated graft.

Referring to FIGS. 1-5, the unitary bifurcated graft 20 is a tube of graft material having two graft sections 22 and 24, and a weakened section 26. Each graft section, 22, 24 has a proximal opening 32, 34 and a distal opening 36, 38. The graft sections 22 and 24 are integral to and monolithic with each other via a portion 28 of the graft material. Preferably, graft sections 22, 24 are tapered, with the taper decreasing from the proximal openings 32, 34 to the distal opening 36, 38, as shown in FIGS. 3-5.

Figure 1:
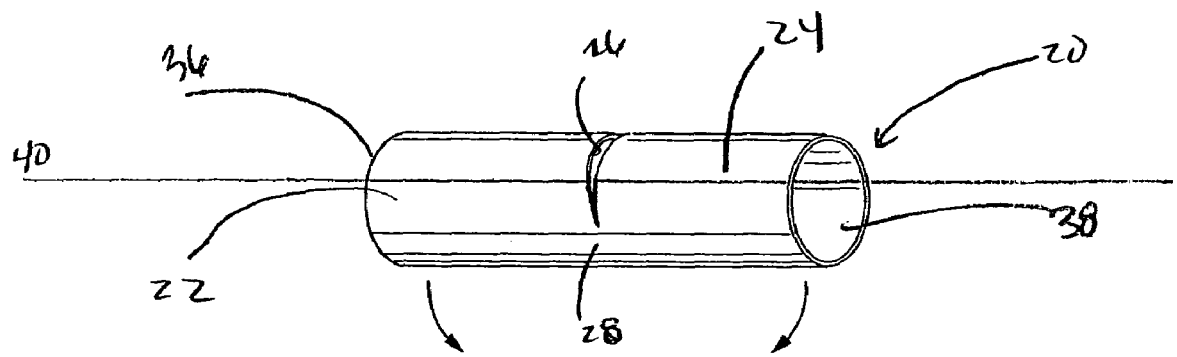
FIG. 1 shows a unitary tubular graft.
Figure 2:
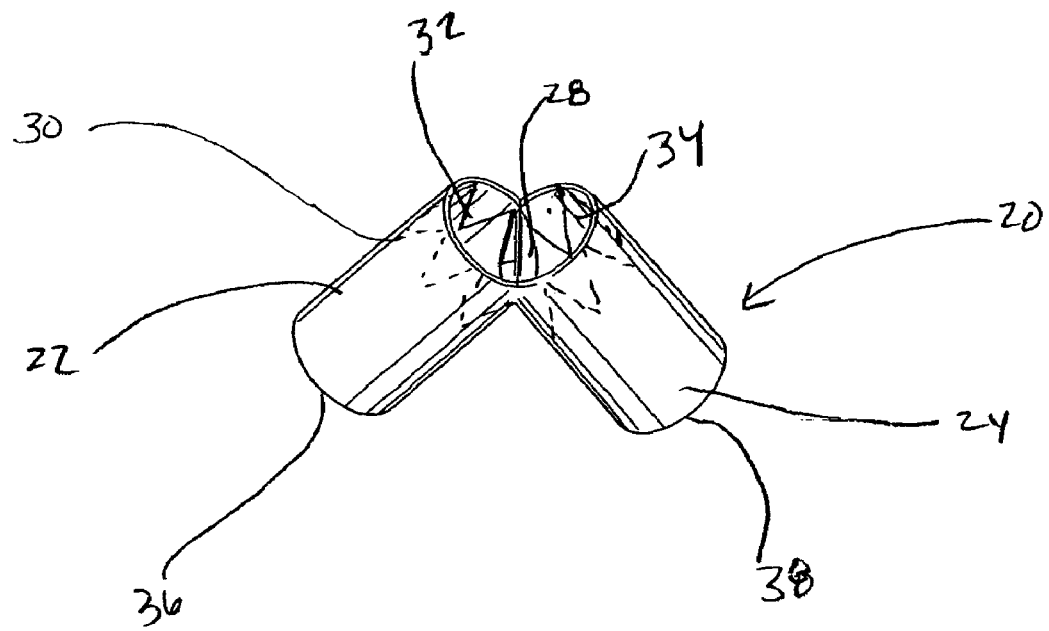
FIG. 2 shows the graft of FIG. 1 formed into a unitary bifurcated graft.

Referring to FIGS. 1 and 3, weakened section 26 may comprise a lateral cut that runs perpendicular to the longitudinal axis 40 of the graft 20. Referring to FIG. 4, weakened section 26 may also comprise a series of tearable perforations 42 that may be broken to form graft sections 22, 24. Weakened section 26 may be of any suitable length sufficient to create graft sections 22, 24, without separating graft sections 22, 24 into discrete components.

The diameter of graft sections 22, 24 may range from 8 mm to 24 mm, and the length may range from 15 mm to 125 mm. The distance between the proximal openings 32, 34 of the graft sections 22, 24 may be approximately double the thickness of the graft material and, thus, is dictated by the thickness of the graft material used for graft 20. For example, the distance between the proximal openings 32, 34 of the graft sections 22, 24 may be from about 0 mm to about 10, preferably, from about 0 mm to about 6.

Figure 8:
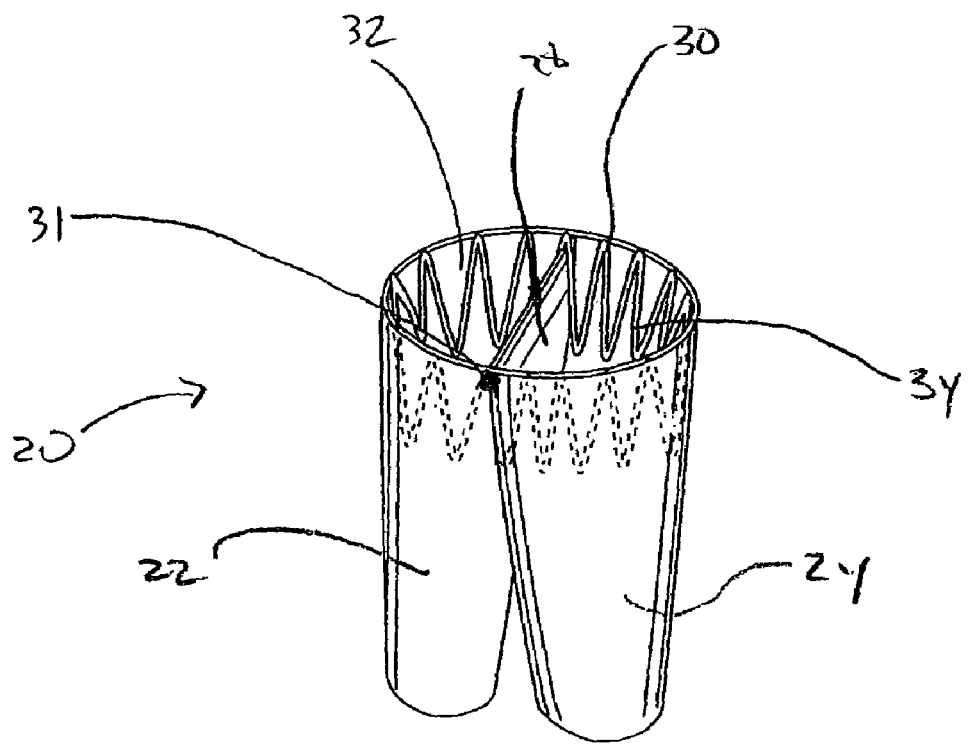
FIG. 8 is a perspective view of the graft of either FIG. 3 or 4 formed into a unitary bifurcated graft and having an internal stent at the proximal end.
Figure 9:
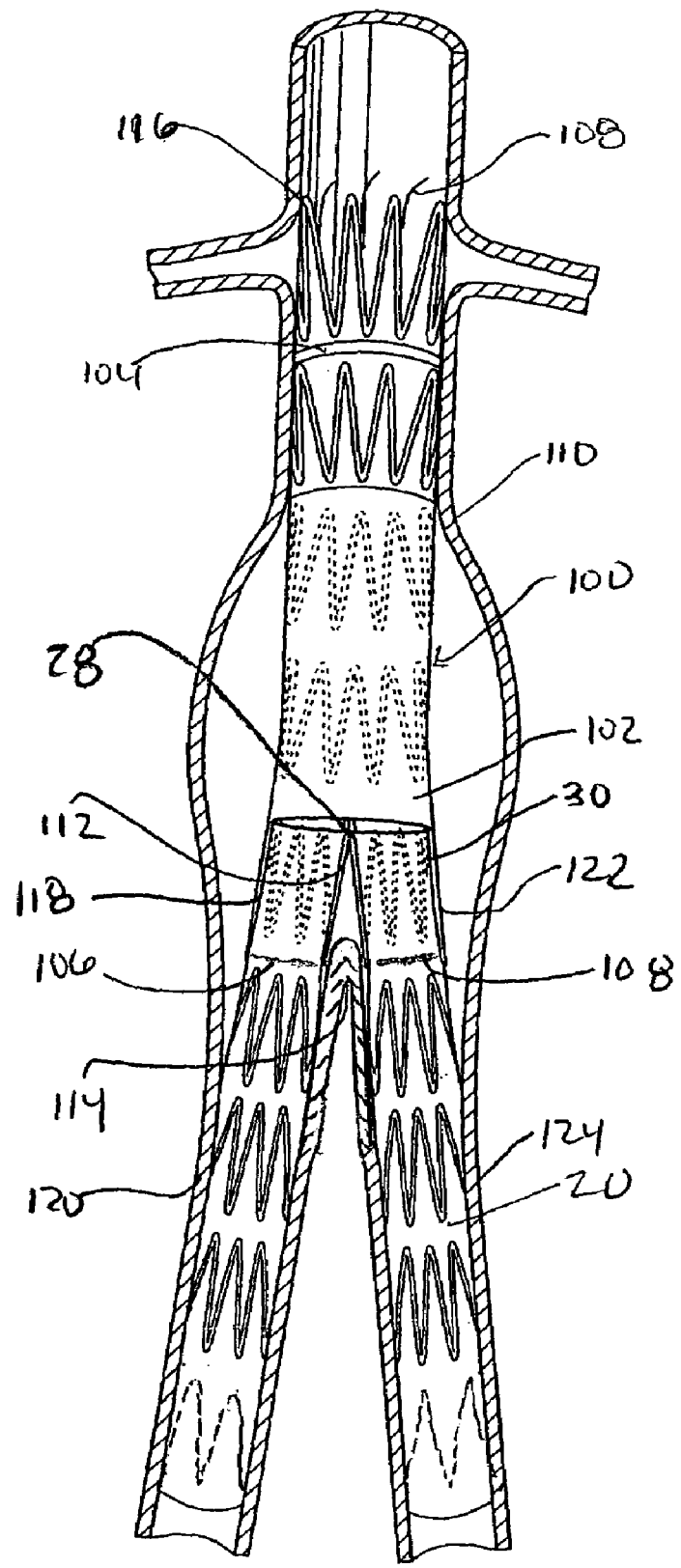
FIG. 9 shows an example of a prosthesis system with a bifurcated main body prosthesis and a unitary bifurcated graft.

Each graft section 22, 24 may contain at least one stent 30 (FIGS. 6-9) attached to the graft 20. Referring to FIG. 9, a stent may be attached to the graft at each of the proximal openings 32, 34 of graft sections 22, 24. In one embodiment, stents 30 (as shown in FIG. 9) may be attached to the inner periphery or outer periphery of each of the proximal openings 32, 34. Alternatively, a single stent may be attached to the inner periphery (FIG. 8) or outer periphery of the combined proximal openings 32, 34.

The graft material of the graft 20 is a biocompatible material. Preferably the biocompatible material is in the form of a fabric that is impermeable to liquids, including blood or other physiological fluids. Examples of biocompatible materials include polyesters, such as poly(ethylene terephthalate), and fluorinated polymers, such as polytetrafluoroethylene (PTFE) and expanded PTFE. Examples of biocompatible polyesters include DACRON (DUPONT, Wilmington, Del.) and TWILLWEAVE MICREL (VASCUTEK, Renfrewshire, Scotland). Examples of biocompatible materials also include extracellular matrix (ECM) materials, such as a purified collagen-based matrix derived from submucosa tissue. Examples of ECM materials include pericardium, stomach submucosa, liver basement membrane, urinary bladder submucosa, tissue mucosa, and dura mater. A specific example of an ECM material is small intestinal submucosa (SIS), such as is described in U.S. Pat. No. 6,206,931, which is incorporated herein by reference.

The graft material may be made of a single material, or it may be a blend, weave, laminate or composite of two or more materials. The graft material may also include other additives, such as plasticizers, compatibilizers, surface modifiers, biological materials such as peptides and enzymes, and therapeutic agents such as drugs or other medicaments.

The graft material may be secured to one or more stents by any means known. For example, standard surgical suturing techniques may be used to secure the graft material to a stent. A stent may be positioned on the interior of the tubular graft material, or on the exterior of the graft material. A stent also may be secured to one of the openings of the tubular graft material such that the stent extends from the material. A stent extending from the graft material can be secured to the interior and/or the exterior of the material. For example, a stent may be sandwiched between two layers of graft material, or a graft may be sandwiched between two layers of stents, and this stent may also be secured by sutures. Examples of suture material include PROLENE® (5-0).

Figures 6, 7:
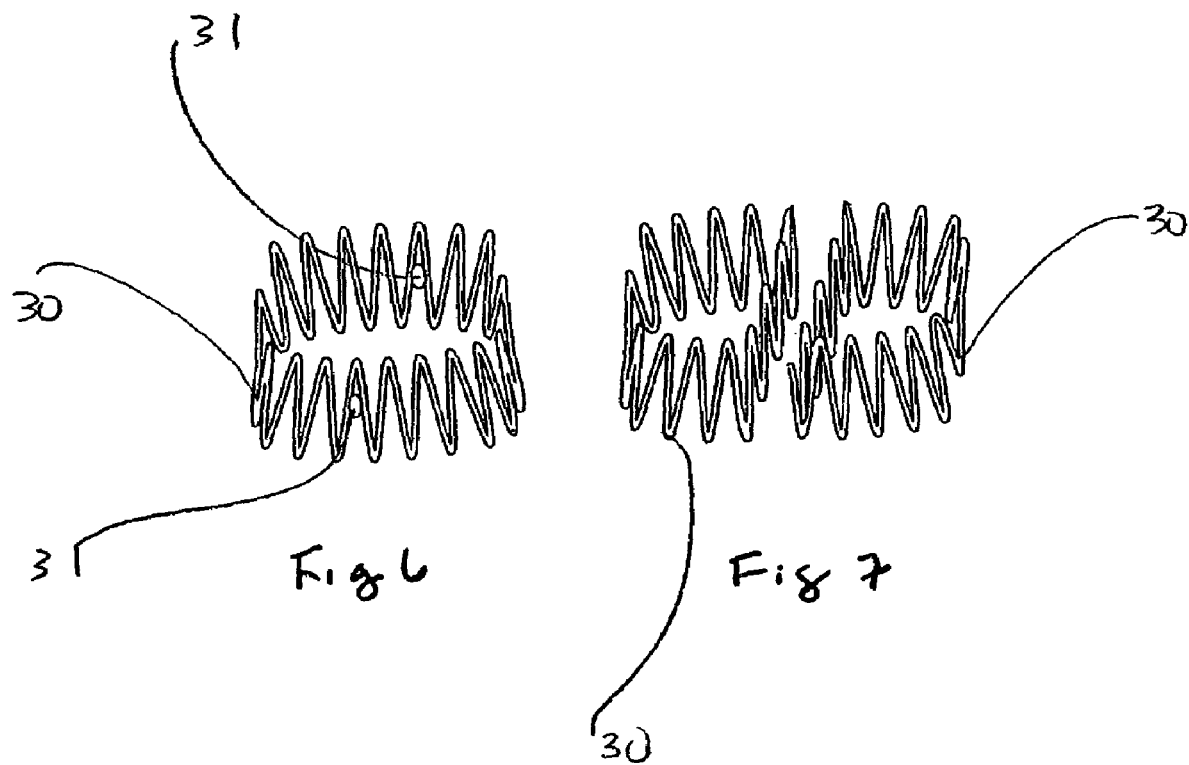
FIGS. 6 and 7 show stents useful in the grafts of the invention.

Stents 30 may have a wide variety of configurations and may be balloon-expandable or self-expanding. Stents 30 may have a circular cross-section, as shown in FIG. 6, when fully expanded, so as to conform to the generally circular cross-section of a body lumen. Alternatively, stents 30 placed at the proximal openings 32, 34 of the graft sections 22, 24 may be semi-circular, as shown in FIG. 7.

Stents 30 useful in the graft sections 22, 24 may be of any suitable configuration known in the art. In one embodiment, stents 30 may be discrete stents having a zig-zag configuration in which straight struts are set at angles to each other and are connected by acute bends. The struts are thus connected into an endless loop, forming a generally tubular structure. Discrete zig-zag stents are also referred to as Gianturco stents or Z-stents. A specific example of a Z-stent is the Z-STENT available from COOK, INC. (Bloomington, Ind.). In another example, the stents may contain individual stent segments that are connected to provide an elongated, flexible stent. The individual stent segments can have a variety of configurations, including the zig-zag configuration. A specific example of a connected zig-zag stent is the ZILVER™ stent available from COOK, INC.

Stents 30 may be made of any rigid biocompatible material, such as metal, plastic or ceramic. Preferably the stents are made of a metal, such as stainless steel, nitinol, and other biocompatible alloys. Stents may be equipped with one or more barbs to secure the prosthesis to the vessel wall or to another component of the prosthesis. If the stent is secured to the graft material by suturing, the sutures may be positioned along struts and/or at bends within the stent. For stents having a zig-zag configuration, it may be desirable to employ two sutures at each bend of the stent to further increase the stability of the connection, as described in United States Publication No. US 2004/0054396A1, which is incorporated herein by reference.

Graft portion 28 retains the graft sections 22, 24 within a minimum distance of each other and allows for a one-piece graft construction without the need for connecting one leg to another. The graft portion 28 is integral and monolithic with the graft materials of each of the graft sections 22, 24. The term "monolithic" means that graft portion 28 is made from the same piece of material as and cannot be separated from the graft sections 22, 24 under a normal use environment without damaging or destroying the unitary graft 20. Graft portion 28 may include reinforcing material at graft portion 28, including additional reinforcing material, sutures, wire or the like.

The dimensions of graft portion 28 and each of the graft sections 22, 24 are determined by the intended use of the unitary graft 20. Ideally, the graft 20 is precisely constructed so as to provide the optimum fit of the prosthesis assembly with the vasculature to be treated. The dimensions of the vasculature may be determined by a variety of methods, including intraoperative intravascular ultrasound (IVUS) and radiologic studies such as computerized tomography (CT), magnetic resonance imaging (MRI), angiography. Graft 20 may also be constructed so as to have a range of discrete sizes. In this way, the graft 20 can be kept in stock for use with other stock components for emergency treatments. This general type of system is described, for example in U.S. Patent Application Publication 2002/0198587 A1.

One of the possible uses of graft 20 is as a component of a prosthesis assembly for treatment of a weakened section of a blood vessel such as an aortic aneurysm. As shown in FIG. 9, such an assembly may include the graft 20 and a bifurcated prosthesis 100 having a main tubular body 102 with a proximal opening 104 and two distal openings 106 and 108. The main tubular body 102 of the bifurcated prosthesis 100 is intended to attach to the healthy tissue above the aneurysm 110 near the proximal opening 104 of the prosthesis 100. The two openings 106, 108 at the distal end of the main tubular body 102 form the bifurcation 112 that fits over the iliac bifurcation 114 such that each distal opening 106, 108 is near or within one of the iliac branch arteries. A stent 116 is attached to and extends from the graft material near the proximal opening 104. This stent contains barbs 108 to provide for anchoring of the prosthesis above the aneurysm 110. One limb 118 may be deployed near or in the ipsilateral iliac artery 120, and the other distal limbs 122 may be deployed near or in the contralateral iliac artery 124. The limbs 118, 122 may be of equal or differing lengths. The limbs 118, 122 may be provided with one or more internal and/or external stents.

The proximal openings of each graft section can contain either an internal stent or an external stent. Internal stents are preferred for the terminal ends of the graft sections, as this may provide for enhanced sealing between the vessel wall and the prosthesis.

Figure 10:
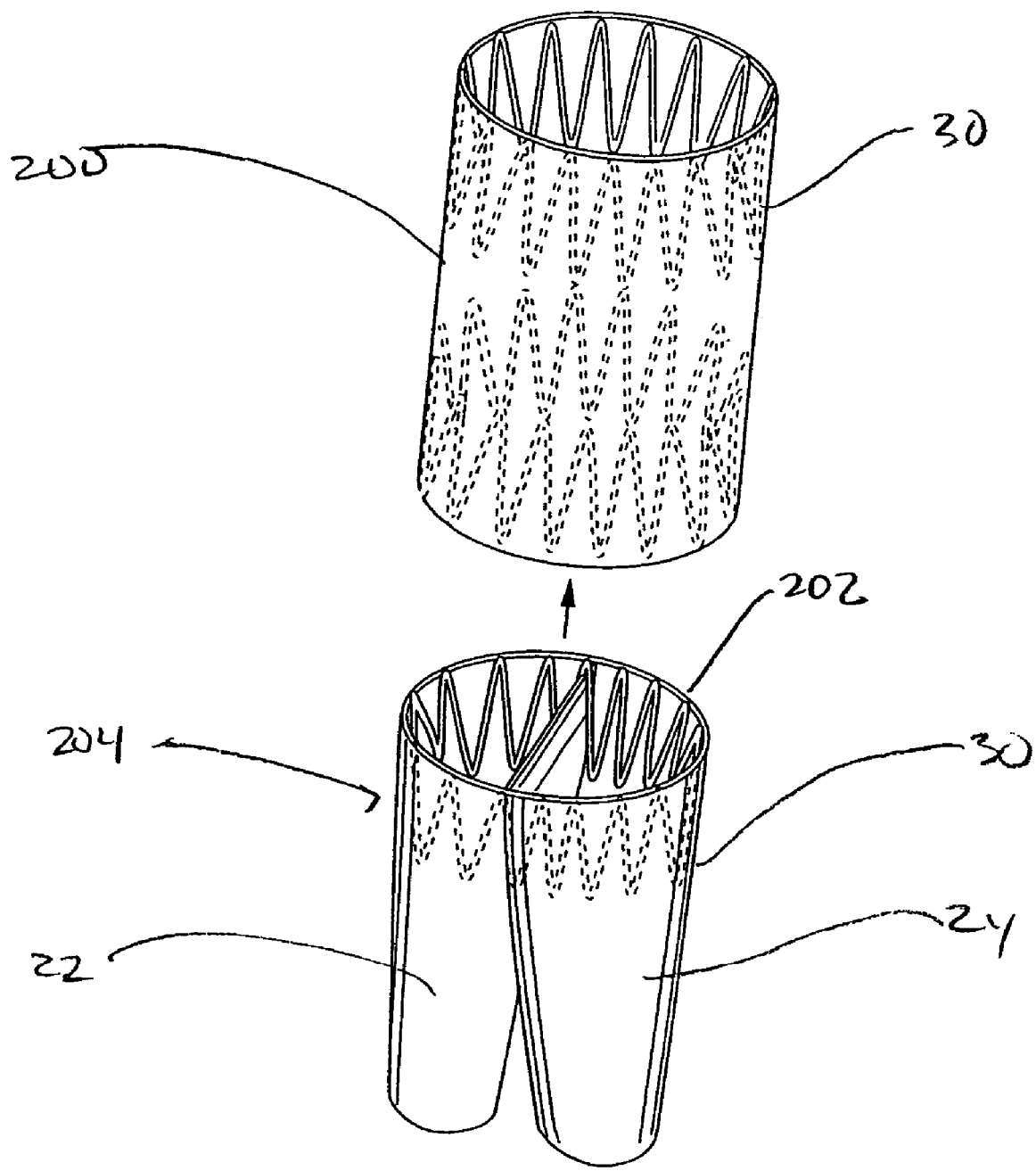
FIG. 10 shows an example of a prosthesis system with a tubular main body prosthesis and a unitary bifurcated graft.

In an alternative embodiment, shown in FIG. 10, the main body 200 of the prosthesis assembly is a cylindrical or tapered tube into which the proximal end 202 of the graft 204 fits in a sealing relationship.

In the treatment of aortic aneurysms, the desired dimensions of prosthesis assembly are determined by the dimensions and condition (i.e. healthy or aneurysmal) of the iliac arteries and by the dimensions of the prosthesis with which the graft 20 will coordinate.

The length of the graft sections and the number of stents contained within the sections can vary independently. For example, a bifurcated main body may have a longer distal leg and a shorter distal leg. A unitary bifurcated graft according to an aspect of the invention for use with this bifurcated prosthesis may have a shorter graft section and a longer graft section. Preferably the shorter graft section contains at least an internal stent at the proximal opening and another internal stent at the distal opening.

Graft 20 can be delivered to a treatment site using a variety of endovascular techniques. In treating aortic aneurysms, a catheter-based introducer can be used to insert a compressed prosthesis into the body through a femoral artery and then into the aorta. The introducer may be similar to those described in WO 03/53761 and in US2002/0198587. The introducer may also comprising a deflecting tip catheter.

A compromised section of a blood vessel may be repaired inserting into the comprised section of the vessel a bifurcated prosthesis comprising a main tubular body having a single proximal opening, a first distal opening and a second distal opening. A unitary tubular graft having a first tube section, a second tube section, a weakened section between the first and second tube sections, is then introduced into a first iliac artery. At least a first section of the tubular graft is passed through the first distal opening of the main tubular body, into the main tubular body and advanced into and through the second distal opening of the main body and partially into the second iliac artery. The weakened section may be positioned approximately adjacent the main body bifurcation with the weakened section opposed the bifurcation. Positioning of the weakened section may be facilitated by one or more markers positioned at or near the weakened and viewed by any means known in the art. Preferably, the marker is radiopaque and viewable by fluoroscopy. The marker may be of any material that provides suitable radiopacity including, but not limited to gold silver, titanium and the like. The radiopaque marker may be positioned anywhere on the graft. For example, as shown in FIG. 6, radiopaque markers 31 may be positioned on stent 30 on opposing sides of stent 30. Alternatively, as shown in FIG. 8, radiopaque marker 31 may be positioned at or near graft portion 28 on one or both sides of the graft. One or more radiopaque markers may be positioned at or near the weakened section to indicate the position of the weakened section and to facilitate proper placement of the weakened section at or near the bifurcation.

After positioning the weakened section at or near the bifurcation the graft may be bent or separated at the weakened section sufficient to form two adjacent legs and two leg openings at the weakened section. The graft sections may then be expanded such that the first section engages the second distal opening of the main body and the second iliac artery and the second section engages the first distal opening of the main body and the first iliac artery.

Figure 11:
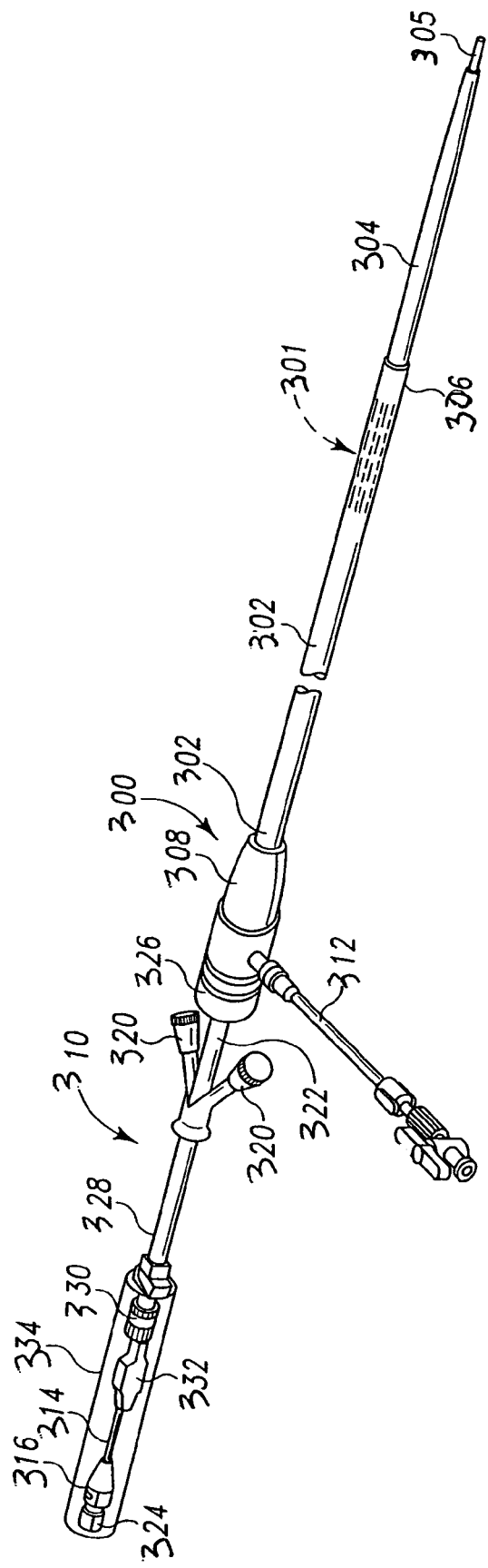
FIG. 11 shows an introducer containing a unitary bifurcated graft during deployment within an aortic aneurysm.

Referring to FIG. 11, an example of an introducer 300 for an graft 301 includes a delivery sheath 302, tapered dilator 304 at proximal end 306, and a fitting 308 at distal end 310 of the delivery system. Inner cannula 314, which is connected to handle 316, extends completely from the tapered dilator 304 to distal end 310. Joined to the side of fitting 308 is an injection system 312, for saturating the prosthesis with anticoagulant heparin or other agents prior to deployment, and optionally for the injection of contrast medium or other agents after deployment.

Referring still to FIG. 11, the introducer 300 also includes check-flow valve 326, pusher 328, pusher fitting 330 and pin vise 332, all of which are covered with a protective tube 334. The protective tube 334 covers the distal end components during handling and is removed prior to use. Tabs 320 are provided at the distal end of short sheath 322, for peeling away the sheath prior to use. Sheath 322 protects the patency of the introducer lumen at the check-flow valve during shipping and handling, and extends only into fitting 308. Stylet 324 extends through cannula 314, through pusher 328 and introducer sheath 302 to a proximal tip 305 that protrudes from the proximal end of the tapered dilator 304. Stylet 324 is also of protective value during shipping and handling and is likewise removed prior to use in the medical procedure.

Figure 12:
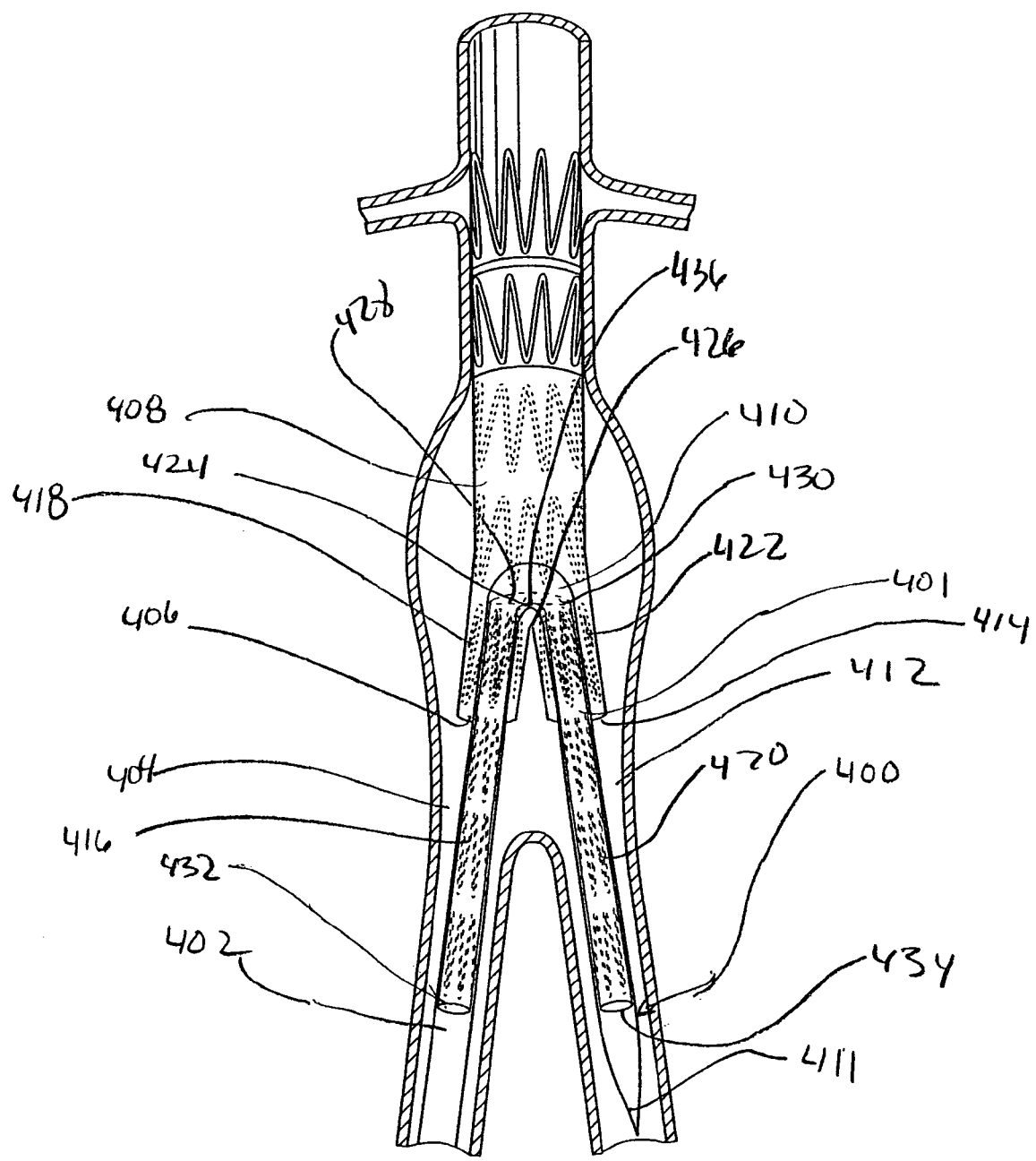
FIG. 12 shows a prosthesis system with a bifurcated prosthesis main body deployed in the aorta and bifurcated unitary graft deployed into the iliac arteries prior to expansion of the bifurcated unitary graft.

Referring to FIG. 12, delivery system 400 for introducing graft 401 is introduced into the patient in delivery sheath 402 by insertion through ipsilateral iliac artery 404 and into the distal opening 406 of a bifurcated prosthesis 408 that has been deployed in the main aorta. The inner cannula 410 is then bent at an acute angle to direct the dilator 411 down the contralateral artery 412 and past the other distal opening 414 of the bifurcated prosthesis 408. At this point, the compressed graft section 416 of graft 401 is within leg 418, graft section 420 is within leg 422, and graft portion 424 spans the bifurcated section 426 of bifurcated prosthesis 408. The delivery sheath 400 can then be pulled back towards the distal end of the delivery system, sequentially releasing graft 401.

As each graft section of the graft is released, that section self-expands and may press against the inner surface of the bifurcated main body or against the vessel wall of the iliac artery. The proximal openings 428 and 430 expand against the distal portions of legs 418 and 422, establishing a friction fit between the graft sections and the bifurcated prosthesis. Thus, the graft sections 416 and 420 function as leg extensions for the prosthesis assembly. The distal openings 432 and 434 of graft 401 engage the vessel wall in the iliac arteries and function as the distal ends of the legs. The attachment of graft 401 at the implantation site and its sealing engagement to the bifurcated prosthesis and to the vessel walls may be further enhanced by inflating a molding balloon at each site to fully expand the graft to press against the bifurcated prosthesis and/or the vessel wall.

As shown in FIGS. 9 and 12, the graft portion 28 and 436 (respectively in FIGS. 9 and 12) is approximately adjacent the bifurcation within the main prosthesis, and the graft material of each graft section overlaps with the graft material of the main prosthesis. Delivery of the complete prosthesis assembly is simplified since the graft sections are part of a single unitary component. In addition, this prosthesis system provides a reduced risk of leg extension separation due to the counterbalancing of forces on the two iliac leg grafts.

Throughout this specification various indications have been given as to the scope of the invention but the invention is not limited to any one of these but may reside at two more of these combined together. The examples are given for illustration only and not for limitation.

The invention claimed is:

1. An endoluminal graft comprising:
 a tube of graft material having a first end, a second end, and a frangible section disposed between the first and second ends;
 the tube including a first leg having a proximal end disposed adjacent one side of the frangible section and a distal end disposed at the first end of the tube, and a second leg integral with and adjacent to the first leg, the second leg having a proximal end disposed adjacent the other side of the frangible section and a distal end disposed at the second end of the tube;
 where the frangible section comprises a series of perforations in the graft material perpendicular to a longitudinal axis of the tube and extending at least partially circumferentially about the tube;
 where the frangible section connects the first leg and the second leg so that the first and second legs share a common lumen;
 where each of the legs comprises at least one expandable stent secured to the graft material; and
 where the frangible section is at least partially breakable upon the application of a bending force perpendicular to the longitudinal axis of the tube.

2. The graft of claim 1 where the expandable stents are self-expanding.

3. The graft of claim 1 where each of the first and second legs comprises an internal stent at the proximal end.

4. The graft of claim 1 where each of the first and second legs comprises an internal stent at the distal end.

5. The graft of claim 1 comprising a stent about a combined periphery of the proximal ends.

6. The graft of claim 1 comprising at least one radiopaque marker.

7. The graft of claim 6 where the at least one radiopaque marker is adjacent a portion of the graft between the proximal ends.

8. The graft of claim 7 where the at least one radiopaque marker is located at the frangible section.

9. The graft of claim 1 where the first leg is monolithic with the second leg.

10. The graft of claim 1, further comprising a second graft having a proximal end and a distal end, where the tube of graft material is insertable into at least one of the proximal and distal ends of the second graft to extend the second graft.

11. The graft of claim 1, further comprising a second graft having a proximal end and a distal end, where the tube of graft material is insertable into at least one of the proximal and distal ends of the second graft to extend the second graft.

12. An endoluminal prosthesis, comprising:
a main body having a proximal end and a distal end and comprising a bifurcation, a first limb, and a second limb; and
a tube of graft material insertable into at least one of the proximal and distal ends, the tube of graft material comprising a frangible section, a first leg disposed adjacent one side of the frangible section, and a second leg, integral with and adjacent to the first leg, disposed adjacent the other side of the frangible section;
where the frangible section comprises a series of perforations in the graft material perpendicular to a longitudinal axis of the tube, extends at least partially circumferentially about the tube, and connects the first leg and the second leg so that the first and second legs share a common lumen
where the frangible section is at least partially breakable upon the application of a bending force perpendicular to the longitudinal axis of the tube.

13. The endoluminal prosthesis of claim 12 where the tube is formed from a single tube of graft material and the first and second legs are integral and monolithic with each other.

14. The endoluminal prosthesis of claim 13 where at least a portion of the first and second legs of the tube are within the distal end of the main body.

15. The endoluminal prosthesis of claim 14 where the first leg is disposed in the first limb of the main body and the second leg is disposed in the second limb of the main body.

16. An endoluminal graft comprising:
a tube of graft material having a first end, a second end, and a single, continuous lumen disposed between the first and second ends;
a first expandable stent secured to the graft material and a second expandable stent secured to the graft material; and
a means for at least partially tearing the tube upon the application of a bending force perpendicular to the longitudinal axis of the tube, whereby application of a bending force on the tube separates the tube into:
a first leg portion comprising the first expandable stent and having a proximal end, a distal end disposed at the first end of the tube, and a first lumen disposed between the proximal and distal ends of the first leg portion;
a second leg portion, integral and monolithic with the first leg portion, comprising the second expandable stent and having a proximal end, a distal end disposed at the second end of the tube, and a second lumen disposed between the proximal and distal ends of the second leg portion.

17. The graft of claim 16 where the means for breaking the tube comprises a series of perforations in the graft material perpendicular to a longitudinal axis of the tube and extending at least partially circumferentially about the tube.

* * * * *